US012665057B2

(12) United States Patent
Klamt

(10) Patent No.: US 12,665,057 B2
(45) Date of Patent: Jun. 23, 2026

(54) RENORMALIZATION BY COMPLETE ASYMMETRIC FLUCTUATION EQUATIONS (CAFE)

(71) Applicant: Dassault Systemes Deutschland GmbH, Stuttgart (DE)

(72) Inventor: Andreas Klamt, Waldburg (DE)

(73) Assignee: DASSAULT SYSTEMES DEUTSCHLAND GMBH, Stuttgart (DE)

( * ) Notice: Subject to any disclaimer, the term of this patent is extended or adjusted under 35 U.S.C. 154(b) by 1056 days.

(21) Appl. No.: 17/519,090

(22) Filed: Nov. 4, 2021

(65) Prior Publication Data

US 2022/0148687 A1    May 12, 2022

Related U.S. Application Data

(60) Provisional application No. 63/110,431, filed on Nov. 6, 2020.

(51) Int. Cl.
*G06F 30/20* (2020.01)
*G06F 111/10* (2020.01)
(Continued)

(52) U.S. Cl.
CPC ............. *G16C 60/00* (2019.02); *G06F 30/20* (2020.01); *G06F 2111/10* (2020.01); *G06F 2113/08* (2020.01)

(58) Field of Classification Search
CPC ......... G16C 60/00; G16C 20/30; G06F 30/20; G06F 2113/08
(Continued)

(56) References Cited

U.S. PATENT DOCUMENTS

| 8,244,504 B1 | 8/2012 | Jacobs |
| 2011/0066285 A1 | 3/2011 | Xu et al. |
| (Continued) | | |

FOREIGN PATENT DOCUMENTS

| CN | 109817283 A | 5/2019 |
| CN | 110211642 A | 9/2019 |
| (Continued) | | |

OTHER PUBLICATIONS

Andreas Klamt et. al, COSMOSPACE: Alternative to Conventional Activity-Coefficient Models, Oct. 2002, AlChE Journal, vol. 48 No 10, pp. 2333-2342 (Year: 2002).*
(Continued)

*Primary Examiner* — John E Johansen
(74) *Attorney, Agent, or Firm* — Hamilton, Brook, Smith & Reynolds, P.C.

(57) ABSTRACT

Embodiments simulate liquid mixtures. An embodiment begins by receiving a free energy curve of a liquid mixture comprising two components. Based on the received free energy curve, a partition function describing fluctuations of mole fractions of the two components in the liquid mixture is constructed. In turn, a renormalized free energy curve of the liquid mixture is calculated using the constructed partition function. The behavior of the liquid mixture is then simulated using, i.e., applying, the calculated renormalized free energy curve. Computer automated simulation systems and apparatus are example applications of the inventive method and disclosed techniques.

15 Claims, 9 Drawing Sheets

770 —

(51) Int. Cl.
   *G06F 113/08* (2020.01)
   *G16C 60/00* (2019.01)
(58) Field of Classification Search
   USPC .......................................................... 703/9
   See application file for complete search history.

(56) References Cited

U.S. PATENT DOCUMENTS

| | | | |
|---|---|---|---|
| 2012/0095736 A1* | 4/2012 | Wang ..................... | G16C 20/30 |
| | | | 703/2 |
| 2015/0317459 A1 | 11/2015 | Farhi et al. | |
| 2017/0083688 A1 | 3/2017 | Chen et al. | |
| 2018/0004863 A1 | 1/2018 | Zuo et al. | |

FOREIGN PATENT DOCUMENTS

| | | |
|---|---|---|
| CN | 111862264 A | 10/2020 |
| KR | 10-2020-0119575 A | 10/2020 |
| WO | 2014027196 A2 | 2/2014 |
| WO | 2014085902 A2 | 6/2014 |
| WO | 2017/121641 A1 | 7/2017 |

OTHER PUBLICATIONS

Anwesa Karmakar et. al, Solubility model of metal complex in ionic liquids from first principle calculations, May 29, 2019, Royal Society of Chemistry; pp. 18503, 18507, 18508, 18523 (Year: 2019).*
Extended European Search Report for EP 21204756.7 dated Mar. 30, 2022 titled "Renormalization by Complete Asymmetric Fluctuation Equations (CAFE)".
Andreas Klamt et al: "COSMOSPACE: Alternative to conventional activity-coefficient models", Alche Journal, John Wiley & Sons, Inc, US, vol. 48, No. 10, Oct. 16, 2002 as listed on document, pp. 2332-2349.
Yoshio Iwai, "The 100-year History, Current Situation and Future Development of the Calculation Methods for Phase Equilibria", Chemical engineering = Chemical engineering of Japan 77 (7), 460-464, 2013.
DOU Shixue, The Structure and Thermodynamic Properties of Silicate Melts, Iron and Steel, No. 05, May 31, 1981.
Feng, C., et al., "Development of the software of predicting the liquid liquid phase equilibrium of polymer hybrid system", Computers and Applied Chemistry, No. 9, Sep. 28, 2010.
Hugang, M., et al., "Comparative Study on Component Activity Predication in S n Based Ternary Liquid Alloys", Journal of Kunming University of Science and Technology (Natural Science Edition), vol. 41, No. 03, Jun. 23, 2016, 8 pages.
Wilson, K. G. Renormalization group and critical phenomena. II. Phase-space cell analysis of critical behavior. Phys. Rev. B, 4, 3184-3205 (1971).
Hohenberg, P. C., and A. P. Krekhov. "An introduction to the Ginzburg-Landau theory of phase transitions and honequilibrium patterns." Physics Reports 572 (2015): 1-33.
Walker, James S., and Chester A. Vause. "Lattice theory of binary fluid mixtures: Phase diagrams with upper and lower critical solution points from a renormalization-group calculation." The Journal of chemical physics 79.6 (1983): 2660-2676.
Yu, Fan, and Jun Cai. "Renormalization Group Approach to Binary Liquid-Liquid Equilibria." Industrial & Engineering Chemistry Research 59.20 (2020).
Klamt, Andreas, Gerard JP Krooshof, and Ross Taylor. "COSMOSPACE: Alternative to conventional activity coefficient models." AlChE journal 48.10 (2002).
Lee, D. D., J. H. Choy, and J. K. Lee. "Computer generation of binary and ternary phase diagrams via a convex hull method." Journal of phase equilibria 13.4 (1992): 365-372.
Klamt, A., "COSMO-RSC: Second-Order Quasi-Chemical Theory Recovering Local Surface Correlation Effects", J. Phys. Chem. A, (2016), 120, 2049-2056.

* cited by examiner

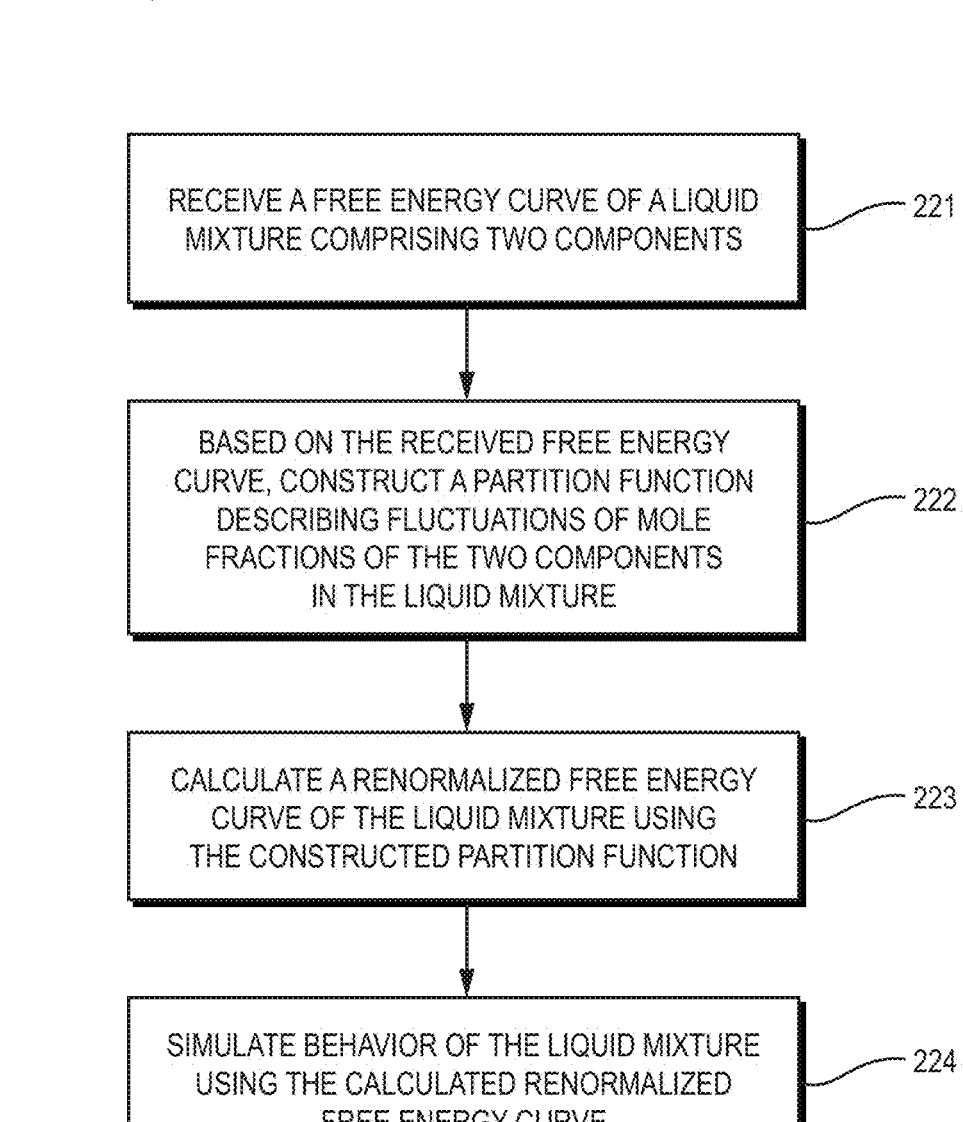

220

RECEIVE A FREE ENERGY CURVE OF A LIQUID
MIXTURE COMPRISING TWO COMPONENTS — 221

BASED ON THE RECEIVED FREE ENERGY
CURVE, CONSTRUCT A PARTITION FUNCTION
DESCRIBING FLUCTUATIONS OF MOLE
FRACTIONS OF THE TWO COMPONENTS
IN THE LIQUID MIXTURE — 222

CALCULATE A RENORMALIZED FREE ENERGY
CURVE OF THE LIQUID MIXTURE USING
THE CONSTRUCTED PARTITION FUNCTION — 223

SIMULATE BEHAVIOR OF THE LIQUID MIXTURE
USING THE CALCULATED RENORMALIZED
FREE ENERGY CURVE — 224

FIG. 2

RENORMALIZATION BY COMPLETE ASYMMETRIC FLUCTUATION EQUATIONS (CAFE)

RELATED APPLICATION

This application claims the benefit of U.S. Provisional Application No. 63/110,431, filed on Nov. 6, 2020. The entire teachings of the above application are incorporated herein by reference.

BACKGROUND

Simulation and, in particular, computer based simulation of liquids, has become an important part of many industrial development processes. The use of computer based liquid simulation, such as the functionality provided by the method COSMO-RS and the software COSMOTHERM®, is used to develop products, e.g., liquids, in numerous industries, such as pharmaceutical and chemical product industries. Moreover, the results of these liquid simulations are also used to modify or control product manufacturing processes and improve system, e.g., manufacturing, efficiency.

While the use of computer based liquid simulation has become widespread, such methods and systems can benefit from improvements to simulation accuracy.

SUMMARY

Embodiments provide such improvements. In particular, embodiments improve quantitative simulations of mutual liquid solubility and solve problems in computer based simulation of thermodynamic equilibria of liquid systems. Embodiments accurately predict the mutual solubilities of two liquids close to a critical solution temperature.

One such embodiment, which may be referred to herein as CAFE (complete asymmetric fluctuation equation), constructs a partition function based on the total free energy curve $g(x;T)$ of a liquid mixture of two components that covers all possible symmetric and asymmetric linear fluctuations of the mole fraction around the average mole fraction X at a temperature T. Such an embodiment calculates the renormalized free energy curve $g_{ren}(x)$ as a negative logarithm of the constructed partition function multiplied by the thermal energy RT, where R is the universal gas constant. An example embodiment utilizes a scaling parameter X for the temperature T, which is either a universal constant or a universal linear function of properties available from the unrenormalized $g(x;T)$ curve. To continue, a renormalized liquid-liquid equilibrium (LLE) curve is then calculated from $g_{ren}(x;T)$ using a standard tangent construction method that implements fundamental thermodynamics calculations. In turn, this renormalized LLE curve is used to simulate the liquid mixture.

Another example embodiment is directed to a computer-implemented method for simulating a liquid mixture. The method begins by receiving a free energy curve of a liquid mixture comprising two components. Based on the received free energy curve, a partition function describing fluctuations of mole fractions of the two components in the liquid mixture is constructed. In turn, a renormalized free energy curve of the liquid mixture is calculated using the constructed partition function. Then, the behavior of the liquid mixture is simulated using the calculated renormalized free energy curve. Such simulation application of the calculated or resulting renormalized free energy curve provides advantages and efficiencies heretofore unachieved in simulation technologies.

An embodiment receives the free energy curve in the form of a mathematical representation. Moreover, because the method is computer-implemented, the free energy curve may be received from any point communicatively coupled to the computing device implementing the method. According to an embodiment, the constructed partition function covers symmetric and asymmetric fluctuations of the mole fractions of the two components around an average mole fraction. In an embodiment, the renormalized free energy curve is a negative logarithm of the constructed partition function multiplied by molar thermal energy, RT. In another example embodiment, the renormalized free energy curve is a function of a temperature scaling parameter. In such an embodiment, the temperature scaling parameter can be a constant or a function of properties determined based on the received free energy curve of the liquid mixture.

In an embodiment of the method, simulating behavior of the liquid mixture using the calculated renormalized free energy curve includes predicting liquid-liquid-equilibrium of the liquid mixture using a tangent construction method. The simulation performed using the calculated renormalized free energy curve may be used to predict a variety of different properties of the behavior of the liquid mixture. For example, embodiments may predict critical solution temperature, e.g., lower critical solution temperature and upper critical solution temperature, and/or renormalized equilibrium compositions of the two components, amongst other examples.

An example embodiment determines a more realistic shape of predicted liquid-liquid equilibrium curves for a liquid mixture at different temperatures. Embodiments can be implemented in existing simulation applications and programs, such as COSMOTHERM®, to improve the results, e.g., liquid-liquid equilibrium curves, determined by these existing applications. Embodiments can be employed for liquid processing and screening simulations. Embodiments can be used to determine optimal mixtures and conditions for creating mixtures. Such embodiments can be used across a variety of fields and applications, including chemical and pharmaceutical applications, and any applications where liquid mixture simulation is utilized.

Another embodiment is directed to a system that includes a processor and a memory with computer code instructions stored thereon. In such an embodiment, the processor and the memory, with the computer code instructions, are configured to cause the system to implement any embodiments or combination of embodiments described herein.

Yet another embodiment of the present invention is directed to a cloud computing implementation for simulating a liquid mixture. Such an embodiment is directed to a computer program product executed by a server in communication across a network with one or more clients, where the computer program product comprises instructions which, when executed by one or more processors, causes the one or more processors to implement any embodiments described herein.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 2 is a flowchart of a method for simulating a liquid mixture according to an embodiment.

DETAILED DESCRIPTION

A description of example embodiments follows.

As described above, embodiments of the present invention provide improved computer based simulation of liquid mixtures. Liquid mixtures of chemical compounds usually have temperature ranges, in which both compounds are miscible (form a homogenous solution) at any concentration, and other temperature regions, in which the compounds decompose into two or more sub-volumes (phases) with different compositions. The composition range between the equilibrium concentrations is called the miscibility gap. The coexistence of multiple phases at one temperature is called liquid-liquid-equilibrium (LLE). Usually, the liquids are miscible above an upper critical solution temperature (UCST) and immiscible below the UCST. However, it may also be possible for a liquid to be miscible below a lower critical solution temperature (LCST) and immiscible above the LCST. Herein, the term critical solution temperature (CST) is used to refer to both UCST and LCST.

For a liquid mixture, as long as the temperature is sufficiently far away from the CST, the phases are well separated by a maximum in the total free energy profile (TFEP) of the mixture, i.e. the total free energy of the system as a function of the concentration variables, and the composition of each phase is fixed to the resulting minimum. However, if the temperature of the liquid mixture approaches the CST, the barrier between the minima gets lower and lower and the system, i.e., liquid mixture, can fluctuate in a wide range of composition spaces. This phenomenon, which also appears at the gas-liquid transition of pure fluids, causes long-range composition fluctuations, also called critical density fluctuations. These fluctuations cause an effective smoothing of the free energy landscape and a lowering of the barrier and, thus, the appearance of the critical fluctuations is a self-supporting process, which causes the rapid disappearance of the LLE gap.

Existing analytical models for the calculation of the total free energy (TFE) of liquid mixtures do not include the effects of the critical fluctuations and, therefore, yield UCSTs that are too high and LCSTs that are too low. Moreover, existing methods overestimate the width of the miscibility gap for temperatures close to the CST. This limits the practical use of predictive models in the simulation, development, and optimization of solubilization and separation processes.

Figure 1:
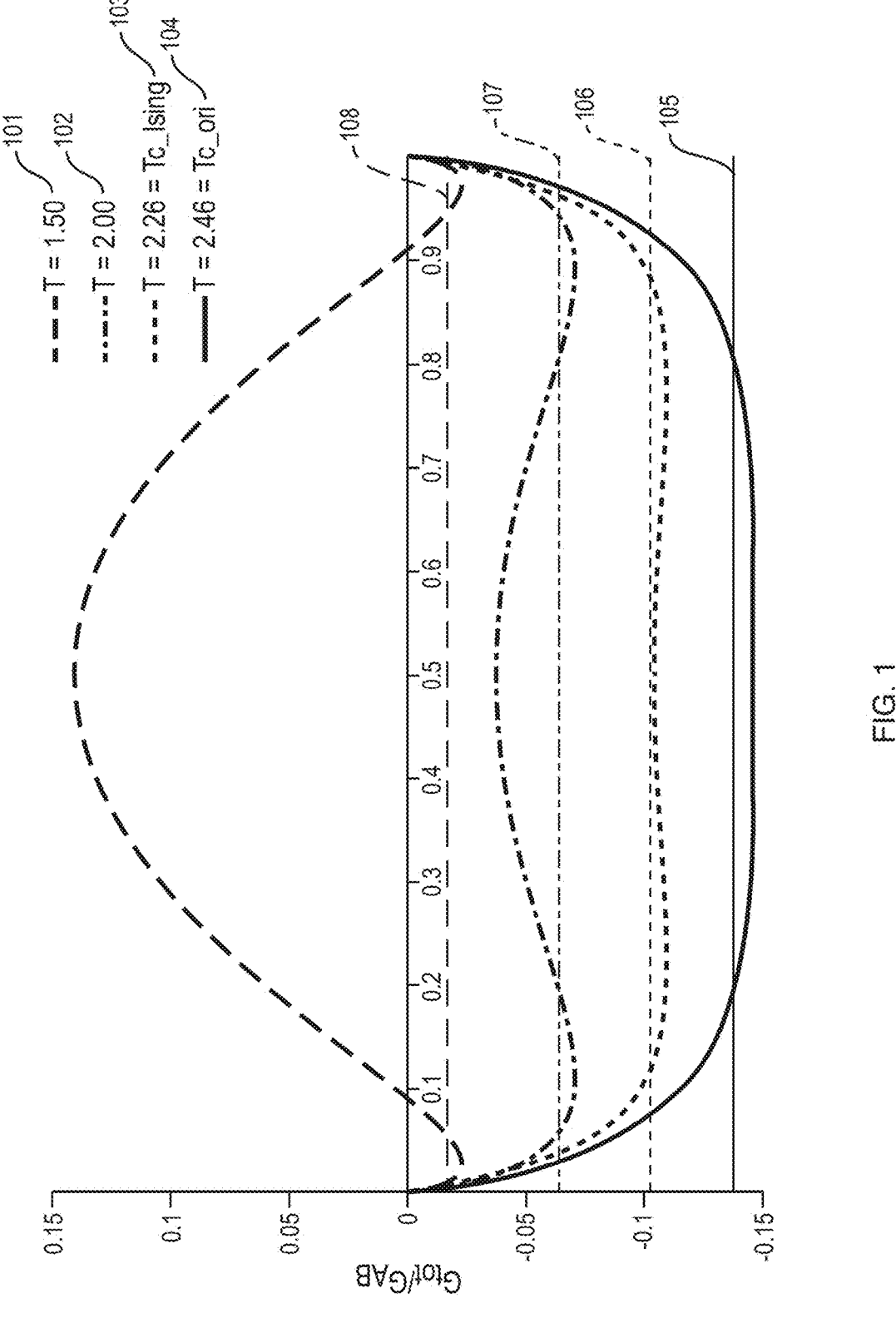
FIG. 1 is a plot showing a free energy profile for a liquid mixture at various temperatures that cannot be simulated using existing methods.

The plot 100 in FIG. 1 illustrates the critical fluctuations that cannot be simulated using existing methods. The plot 100 shows the free energy profile (g(x) curves) for the simple-cubic lattice fluid with nearest neighbor interaction energy $G_{AB}$ at four different temperatures (1.5 curve 101, 2 curve 102, 2.26 curve 103, 2.46 curve 104), quantified in $G_{AB}$ energy units. The g(x) curves 101, 102, 103, and 104 displayed in FIG. 1 are taken from COSMOSPACE and have the mathematical form:

$$\gamma_1 = \sqrt{\frac{1}{\Theta_1} + \frac{1 - \sqrt{1 + 4\Theta_1\Theta_1\omega}}{2\omega\Theta_1^2}} \text{ and } \gamma_2 = \sqrt{\frac{1}{\Theta_2} + \frac{1 - \sqrt{1 + 4\Theta_1\Theta_1\omega}}{2\omega\Theta_2^2}}$$

with $$\Theta_1 = \frac{x_1 A_1}{x_1 A_1 + x_2 A_2} \text{ and } \Theta_2 = \frac{x_2 A_2}{x_1 A_1 + x_2 A_2}$$

being the surface fractions, $A_1$ and $A_2$ being the molecular surface areas, and $\omega$ being given by:

$$\omega = \exp\left\{\frac{2E_{12}}{kT}\right\} - 1$$

where $E_{12}$ is the interaction energy between segments of type 1 and 2. The lines 105, 106, 107, and 108 in the plot 100 indicate the energy level $T/T_{crit}\Delta_{crit}$ relative to the minimum, where $\Delta_{crit}$ is the barrier height at the critical temperature, which roughly corresponds to RT/300.

At temperatures sufficiently below the critical temperature (curve 101), the system is quite confined to the regions close to the minima of the total free energy (the minima of the curve 101), which are well separated by a free energy barrier. At increasing temperatures, thermal energy increases, but more importantly the free energy barrier decreases and the minima get more and more shallow. By that, more and more states in composition space become thermally available, and the system fluctuates between these states. At some temperature, i.e. the true UCST, the barrier gets so small that the fluctuations are no longer confined to the individual minimum regions, and thus no separate regions of different composition, i.e. no separate phases, can be distinguished. At this point, the system (liquid mixture) is macroscopically homogeneous, although there is a small free energy barrier separating the original phases. This barrier only disappears at the UCST of the analytic free energy model, in this case the COSMOSPACE model [6]. When performing simulations of such a liquid, existing methods cannot accurately simulate the fluctuations and, thus, generally inaccurately predict the true UCST.

Methods have been developed in an attempt to correctly determine the simulation, e.g., the correct UCST. The procedures and algorithms for the conversion of LLE-curves from their wrong, analytical shape to the realistic shape resulting from the critical fluctuations, are referred to as renormalization methods. Existing renormalization methods require fitting of a number of adjustable parameters to experimental data of the specific system (liquid mixture) under consideration. Therefore, the existing renormalization methods cannot be used in a predictive manner, i.e., for the prediction of the LLE curves and CSTs of systems which have not been explored experimentally before.

The problem of the quantitative description of the mutual solubilities of liquids close to the upper (or lower) critical solution temperatures, UCST or LCST, respectively, is a longstanding problem known for more than a century [1-3]. All analytic free energy approaches, which often give a reasonable description of the solubility curves as a function of temperature, also called LLE (liquid-liquid equilibrium) curves, for temperatures below 90% of the UCST, strongly fail above this limit. The closure of the predicted LLE curves is much too slow with a critical exponent of 0.5, typically yielding a predicted UCST which is about 10% high, which can easily be 30-50 K. Meanwhile, the experimental LLE curves close very rapidly with a critical exponent of ~0.32. For practical application in chemical engineering, e.g. the development of separation processes for chemicals, such inaccurate predictions are often a hindrance for using prediction methods.

Many interpolative methods have been developed, partly based on complicated theories, such as Renormalization Group theory by Ginzburg and Landau [4]. However, these existing methods require many experiments of the same system in order to fit the numerous model parameters to the experimental data. Furthermore, even with many parameters, it is not trivial to describe the unusual behavior with the critical exponent of 0.32 adequately. Most approaches, which are accurate close to the UCST, fail in the cross-over region to the analytically well described region.

Molecular simulation in both variants, molecular dynamics simulations and Monte Carlo Simulations are able to describe the critical behavior if sufficiently large systems are simulated for a very long time. However, this requires dramatically long simulation times. Furthermore, the thermodynamic accuracy of such force-field-based simulation approaches is typically much lower than the accuracy of analytic free energy models. Therefore, such simulations are not at all of practical interest for industrial applications, i.e., simulation, development, and manufacturing of real-world liquid mixtures.

A predictive method, which can be efficiently applied to free energy curves resulting from a good predictive free energy model, in order to provide robust, improved, LLE predictions close to the UCST, without using any experimental data of the system, is still missing.

Embodiments of the present invention address the foregoing shortcomings in the art and provide such functionality. FIG. 2 is a flowchart of one such computer implemented method 220 for simulating a liquid mixture. The method 220 starts at step 221 by receiving a free energy curve of a liquid mixture comprising two components. Because the method 220 is computer-implemented, the free energy curve may be received at step 221 from any point communicatively coupled to the computing device implementing the method 220. The curve received at step 221 may pertain to any binary liquid mixture known in the art and, likewise, the two components may be any components known in the art. For example, cylclooctane and pentafluorobutane, amongst other examples. In an embodiment of the method 220, the free energy curve received at step 221 is in the form of a mathematical representation. For example, the free energy curve received at step 221 (an unrenormalized free energy curve) may be in the form:

$$g(x_1) = -kT(\ln x_1 + \ln \gamma_1 + \ln x_2 + \ln \gamma_2)$$

where k is the Boltzmann constant, T is the temperature, $x_1$ and $x_2$ are the mole fractions, and $\gamma_1$ and $\gamma_2$ are the activity coefficients of the of the two components. The latter may be taken from any analytic activity coefficient model such as NRTL, UNIQUAC, Wilson, and van Laar, amongst others, or from the COSMOSPACE model. The logarithmic activity coefficient may be taken from the NRTL model (Non-Random-Two-Liquid-Model, Renon H., Prausnitz J. M.: Local Compositions in Thermodynamic Excess Functions for Liquid Mixtures, AIChE J., 14(1), S. 135-144, 1968). If the logarithmic activity coefficient is taken from the NRTL model, the mathematical expression for the logarithmic activity coefficient is given by:

$$\ln\gamma_1 = x_2^2\left[\tau_{21}\left(\frac{G_{21}}{x_1 + x_2G_{21}}\right)^2 + \frac{\tau_{12}G_{12}}{(x_2 + x_1G_{12})^2}\right]$$

$$\ln\gamma_2 = x_1^2\left[\tau_{12}\left(\frac{G_{21}}{x_2 + x_1G_{12}}\right)^2 + \frac{\tau_{21}G_{21}}{(x_1 + x_2G_{21})^2}\right]$$

where the $\tau_{ij}$ and $G_{ij}$ are parameters adjusted to the system.

Returning to FIG. 2, at step 222, a partition function describing fluctuations of mole fractions of the two components in the liquid mixture is constructed based on the received free energy curve. In an embodiment of the method 220, the partition function is constructed at step 222 using the functionality described hereinbelow in relation to equations (2)-(7). According to an embodiment of the method 220, the partition function constructed at step 222 using equations (2)-(7) covers or takes into account symmetric and asymmetric fluctuations of the mole fractions of the two components around an average mole fraction.

To continue, at step 223, a renormalized free energy curve of the liquid mixture is calculated using the constructed partition function resulting from or output by step 222. An example of the renormalized free energy curve calculated at step 223 is given by the equation (1) below. According to an embodiment, the renormalized free energy curve calculated at step 223 is a negative logarithm of the constructed partition function multiplied by molar thermal energy RT. In yet another example embodiment, the renormalized free energy curve calculated at step 223 is a function of a temperature scaling parameter. In such an embodiment of the method 220, the temperature scaling parameter can be a constant or a function of properties determined based on the free energy curve of the liquid mixture received at step 221.

At step 224, the behavior of the liquid mixture is simulated using the calculated renormalized free energy curve from step 223. In an embodiment of the method 220, simulating behavior of the liquid mixture at step 224 using the calculated renormalized free energy curve includes predicting liquid-liquid-equilibrium of the liquid mixture using a tangent construction method. Embodiments may use any implementation of the tangent construction method known in the art, such as the functionality described in [7] Lee, D. D., J. H. Choy, and J. K. Lee, "Computer generation of binary and ternary phase diagrams via a convex hull method." *Journal of phase equilibria* 13.4 (1992): 365-372. Performing the simulation at step 224 may predict a variety of different properties of the behavior of the liquid mixture. For example, embodiments of the method 220 may predict critical solution temperature, lower critical solution temperature, upper critical solution temperature, and/or renormalized equilibrium compositions, i.e., mutual solubilities, of the two components (compounds), amongst other examples.

In an embodiment of the present invention, e.g., the method 220, renormalization of a free energy function $g(x)$ is described by the following equations:

$$g^{ren}(x) = -\frac{kT}{\lambda}\ln\{Z_{asymm}^{fluct}(x)\} \quad (1)$$

$$Z_{asymm}^{fluct}(x) = \int_0^x dy \int_x^1 dz \exp\left\{-\lambda \frac{\bar{g}(x, y, z)}{kT}\right\} \quad (2)$$

Equation 1 indicates that the renormalized free energy of the system, including the free energy contributions resulting from the critical fluctuations, is calculated from a logarithm of a partition function. According to fundamental statistical thermodynamics, this is even the definition of the free energy. The art of statistical thermodynamics is to find the right way of enumerating the states of a system.

Equation 2 indicates that at a given total composition x, any fluctuation conserves this average concentration. Traditional renormalization theories only consider symmetric fluctuations consisting of two equal regions with compositions $x+\delta$ and $x-\delta$. Since negative compositions are impossible, this definition restricts $\delta$ to the range $0<\delta<x$, which means, that no fluctuation could reach a composition larger than $2\delta$. The other physically unrealistic aspect of the symmetric ($x+\delta$, $x-\delta$) fluctuations usually not taken into account, is the free energy of the cross-over region between the extremes. However, a fluctuation unavoidably has such cross-over regions. Embodiments overcome these problems for the first time in the art by using a two dimensional representation of the fluctuations, characterized by their extreme compositions $y<x$ and $z>x$, where $\bar{g}(x, y, z)$ is the averaged free energy of the considered fluctuation, based on the underlying analytic free energy model.

For a given set of mole fractions x, y, and z, one of the possible assumptions for the shape of the fluctuation of the free energy $\bar{g}(x, y, z)$ is given by a linear weight function. The shape of the fluctuation of the free energy can also be given by an exponential weight function or a piecewise linear weight function, amongst other examples. In such an embodiment, the free energy is given by the integral of all intermediate mole fractions between y and z with a linear interpolation weight function:

$$\bar{g}(x, y, z) = \int_y^z (w_0 + vu)g(u)du = w_0 \int_y^z g(u)du + v \int_y^z ug(u)du \quad (3)$$

The norm of the weight function is unity (1) and the average composition is x, resulting in equations 4 and 5:

$$\text{with } \int_y^z (w_0 + vu)du = 1 \text{ and } \int_y^z (w_0 + vu)u\,du = x \quad (4) \text{ and } (5)$$

Equations (4) and (5) can be solved analytically, resulting in equations 6 and 7:

$$v = \frac{x - \frac{1}{2}(z + y)}{\frac{1}{3}(z^3 - y^3) - \frac{1}{4}(z + y)(z^2 - y^2)} \text{ and } w_0 = \frac{1}{(z - y)} - \frac{v}{2}(z + y) \quad (6) \text{ and } (7)$$

These equations 1-7 thus describe a complete model for the calculation of the renormalized free energy. The equilibrium compositions can be derived from this model by thermodynamic standard methods, as the search for the two minimum of the the the free energy for symmetric systems, or the tangent line search for asymmetric systems. The above equations have the scaling factor X as the only empirical parameter. $1/\lambda$ may be interpreted as the number of molecules which is required in order to define the composition of a volume region, since a single molecule does not define a composition.

For the examples described below in relation to FIGS. 3-5, $\lambda=80$. It can be interpreted that about 80 molecules build up a sufficient volume to define a composition in composition space. The results in FIGS. 3-5 compare results determined using embodiments of the present invention with results determined using lattice-Monte-Carlo (LMC) techniques.

Figure 3:
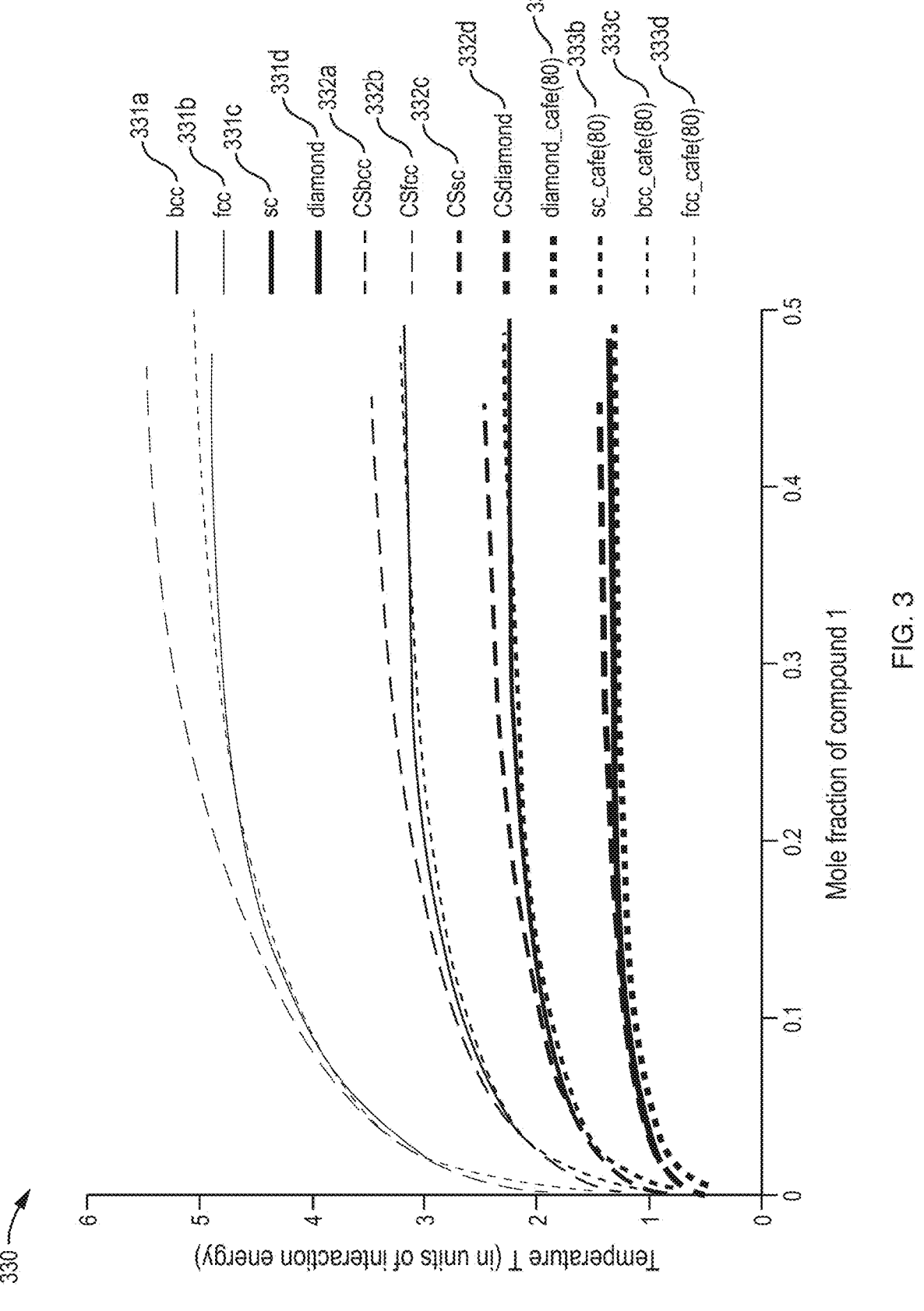
FIGS. 3-5 are plots showing simulation results determined using embodiments and existing methods.

The plot 330 in FIG. 3 shows the results of simulation determining LLE curves for the four Ising-analogues for 3D-lattices diamond, simple-cubic, face-centered cubic (fcc), and body-centered cubic (bcc) with the corresponding coordination numbers, i.e. the number of nearest neighbor molecules, of 4, 6, 8, and 12, respectively. The lines 331a-d are the LMC results, which can be considered as essentially exact in these Ising cases. The lines 332a-d are the results of the corresponding COSMOSPACE calculations. The lines 333a-d are the results generated using an embodiment of the present invention, e.g., CAFE which may include the method 220. The plot 330 shows that embodiments of the present invention provide a good fit of all 4 cases.

Figure 4:
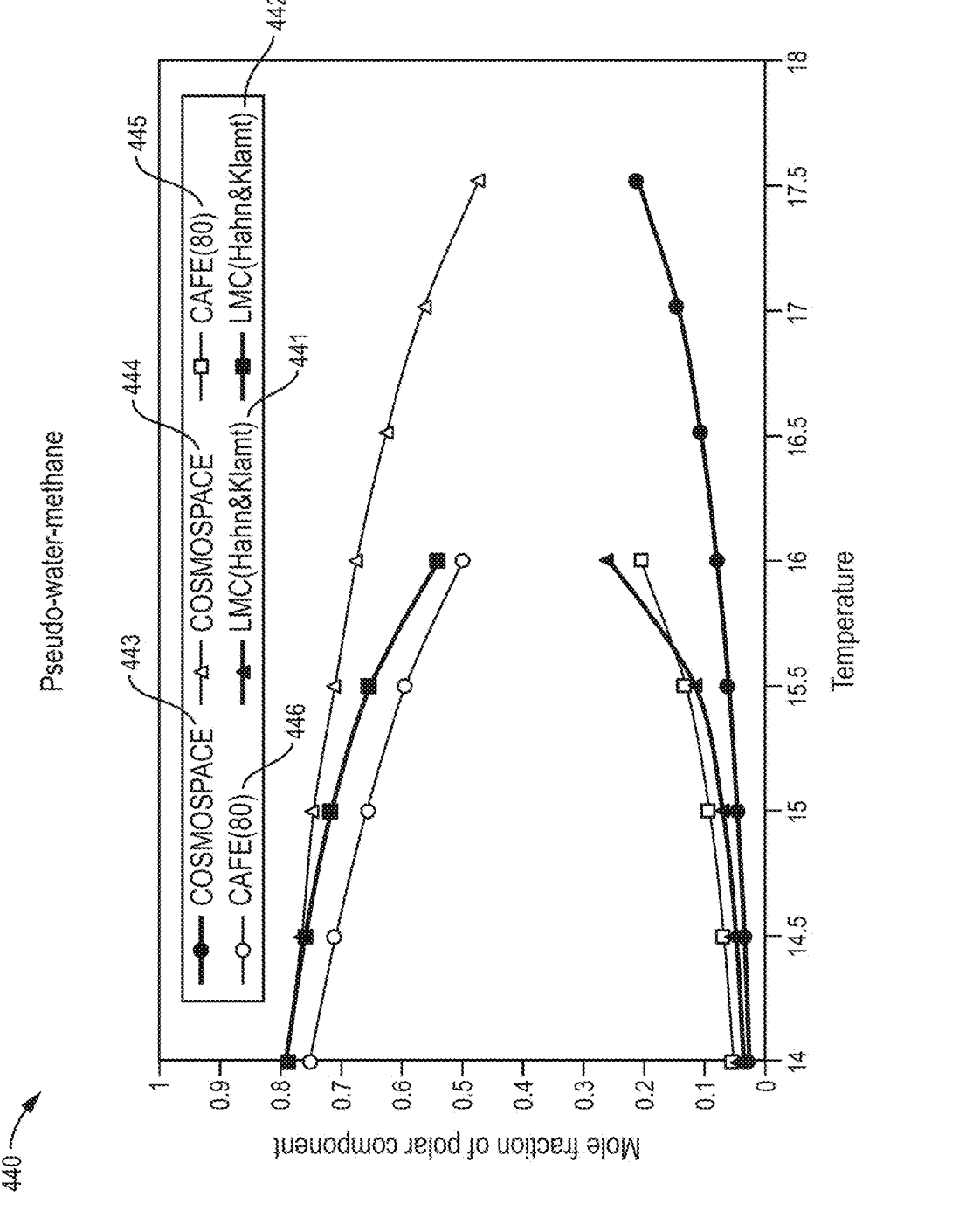

The plot 440 of FIG. 4 shows LLE curves and renormalized LLE curves (determined using embodiments) of a lattice fluid mixture of a polar pseudo-compound (pseudo-water) and a non-polar pseudo-compound (pseudo-methane). In FIG. 4, lines 441 and 442 show LMC results. The unrenormalized free energy curve 444 and LLE curve 443 were produced with the COSMOSPACE method [6]. In the plot 440 the LLE curves 441-446 become asymmetric due to the different interactions. The lines 445 and 446 show the results generated using embodiments of the present invention, i.e., CAFE. Although the results 445 and 446 generated using embodiments of the present invention do not give a perfect match with the LMC results 441 and 442, the results 445 and 446 generated using embodiments give a good quantification of the critical fluctuation effect. It is noted, that these LMC results 441 and 442 also have a substantial uncertainty.

Figure 5:
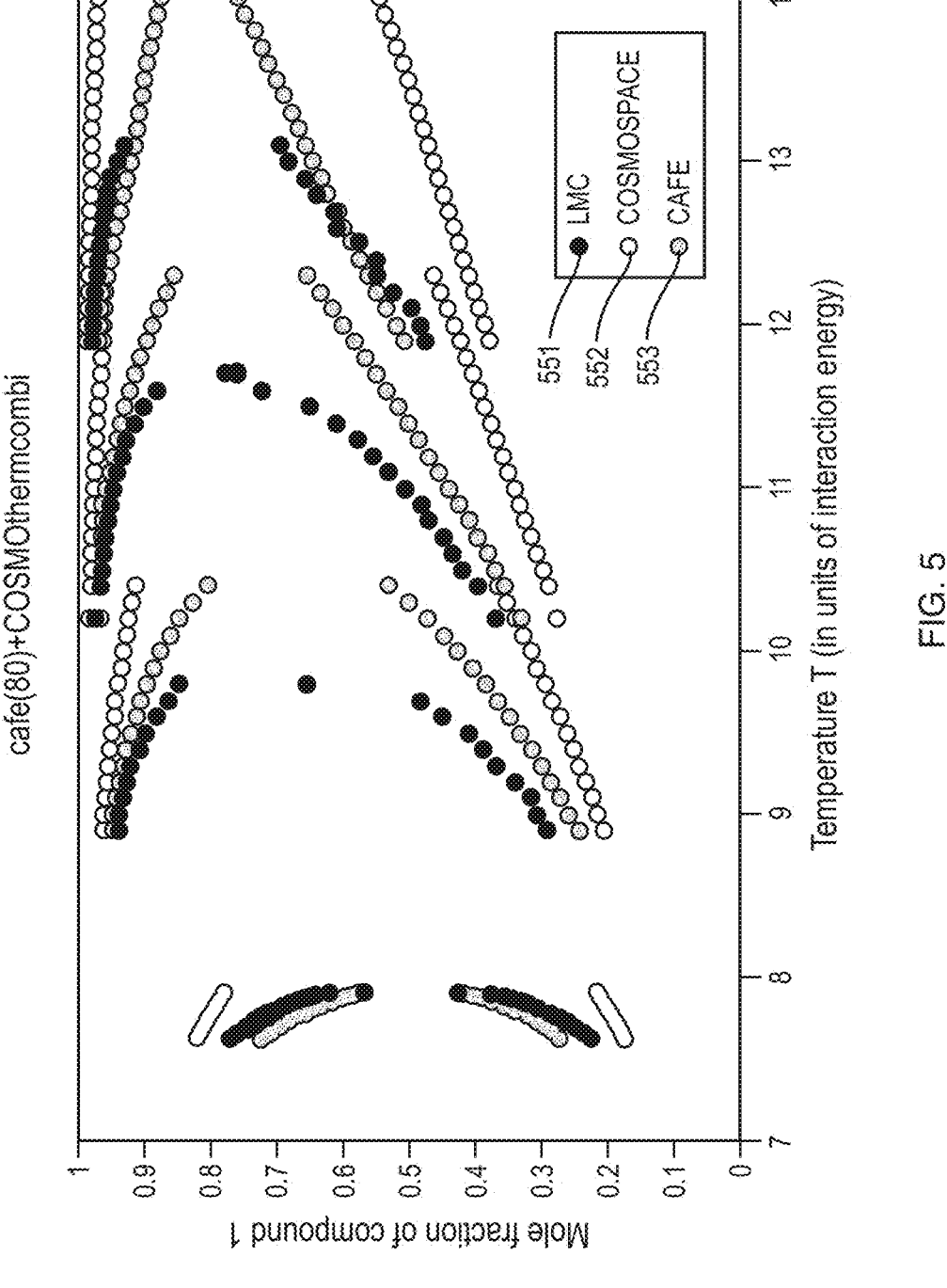

The plot 550 in FIG. 5 illustrates LLE curves for size-asymmetric systems, where compound 1 consists of 1 cube, while compound two is built from 1, 2, 3, and 4 linearly connected cubes, respectively (from left LLE to right LLE). Series 551 indicates LMC results. Series 552 are the COSMOSPACE results, using the standard combinatorial free energy expression of COSMOTHERM®. Series 553 are the CAFE results, i.e., results generated using an embodiment of the present invention, based on the COSMOSPACE+COSMOcombi free energy curves. FIG. 5 shows that the CAFE results (553) are not in perfect agrement with LMC (551), but give a considerable improvement over the COSMOSPACE LLE curves (552) in all cases.

An embodiment corrects, i.e. renormalizes, the predicted critical fluctuation miscibility gap (LLE points) of a liquid mixture based on the total free energy profiles calculated with an accurate predictive pairwise surface segment fluid phase thermodynamics model, which has not been fitted to experimental or Monte-Carlo-Simulation data of the liquid mixture under consideration.

Embodiments can be used predictively without the need for system-specific adjustable parameters. Embodiments are computationally efficient and robust. Embodiments also provide a renormalized total free energy curve, which has numerous applications. For instance, the renormalized total free energy curve may be used to calculate renormalized activity coefficients, which may be used for LLE prediction in thermodynamic simulations, amongst other examples. No methods exist in the art to date for providing such renormalized free energy curves.

Embodiments of the present invention, e.g., the method 220, are computer implemented. As such, embodiments may be implemented using any combination of processors and computer memory programmed in such a way so as to perform the functionality described herein. For instance, an embodiment that implements CAFE renormalization of a free energy function g(x) can be implemented by the following FORTRAN subroutine:

```
FORTRAN subroutine encoding the CAFE renormalization of a free
energy function g(x)
    subroutine CAFErenormalization(nx,x,T,g,scal,gren)
    implicit real*8 (a-h,o-z)
    dimension x(nx),g(nx),gren(nx),rint(2,nx)
c input:
c nx              = number of grid points on mole fraction grid
c scal            = scaling factor for the thermal energy
c x(nx)           = evenspaced array of mole fractions, ranging
                    from 0 to 1.
c T               = Temperature
c g(nx)           = original, i.e. unrenormalized free energy curve
                    (in units of T)
c output:
c gren(nx)        = CAFE renormalized free energy curve (in units
                    of T)
c internal arrays:
c rint(2,nx)      = two arrays for the integrals required for the
                    calculation of the averaged free c energies
        rint=0d0
        do ix=2,nx
          ixm=ix-1
          rint(1,ix)=rint(1,ixm)+(g(ix)+g(ixm))*dx/
          rint(2,ix)=rint(2,ixm)+(g(ix)+g(ixm))*(x(ix)-dx/2)*dx/2
        end do
        do ix=2,nx-1
          flpsum=0d0
          xx=x(ix)
          do iy=1,ix-1
            y=x(iy)
            y2=y*y
            do iz=ix+1,nx
              z=x(iz)
              z2=z*z
              v=(xx-(z+y)/2)/((z**3-y**3)/3-(z+y)*(z*z-y*y)/4)
              w0=1d0/(z-y)-v/2*(z+y)
              efluct=w0*(rint(1,iz)-rint(1,iy))
  &               +v*(rint(2,iz)-rint(2,iy))-g(ix)
              flpsum=flpsum+exp(-efluct/T/scal)
            end do
          end do
          gren(ix)=-T*scal*log(flpsum*dx*dx)*(4*xx*(1-xx))**.1+g(ix)
        end do
        end
```

Hereinbelow, an example application of an embodiment of the present invention is provided. In such an illustrative embodiment, a refrigeration machine producer plans to optimize a refrigeration medium by using mixtures of refrigerants. The process needs to operate in the homogeneous mixture region and, thus, it is crucial for him to forecast the miscibility range of mixtures. An example embodiment can be used to make such a forecast. It is noted that the example implementation described below is but one example use of embodiments and embodiments can be employed for any application where computer-based or computer-automated liquid simulation is desired.

Figures 6A, 6B, 6C:
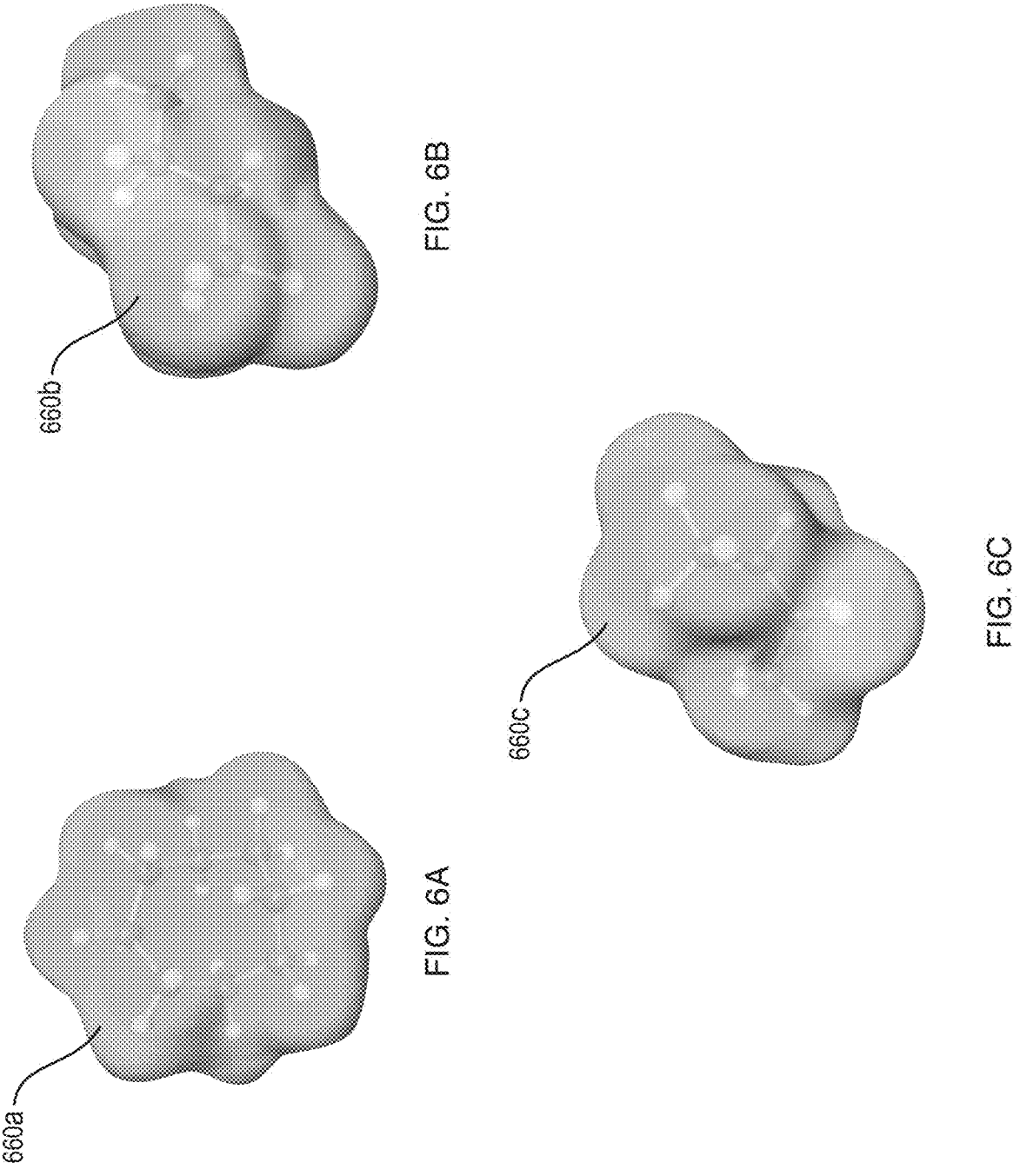
FIGS. 6A-C illustrate surface polarity of compounds that may be simulated using embodiments.

This example embodiment simulates a mixture of alkane cyclooctane with a partially fluorinated compound 1,1,1,3,3-pentafluorobutane (PFB). In such an embodiment, an existing simulation application, e.g., the predictive thermodynamic model COSMO-RS in its commercially available COSMOTHERM® implementation, is used to calculate the liquid-liquid equilibrium (LLE) curve of this binary mixture. Input requires the DFT/COSMO surface polarity information of both compounds, which is calculated with an existing application, such as the quantum-chemical program TURBOMOLE (or equivalent other quantum chemical programs). The results of these calculations are shown in FIGS. 6A-C for both compounds, cyclooctane and PFB. FIG. 6A illustrates the surface polarity 660$a$, i.e., DFT/COSMO surface polarization charge density of cyclooctane. For PFB two relevant intramolecular geometries, so-called conformations, are taken into account. FIGS. 6B and 6C depict the surface polarities 660$b$ and 660$c$, respectively, for the two relevant geometries of PFB.

To continue this illustrative embodiment, a user can load these COSMO results into the COSMOTHERM® program (or other such program to calculate LLE) and select the LLE calculation panel. A start temperature for the LLE search is then set (in the example −100° C.) and the COSMOTHERM® program automatically calculates the unrenormalized LLE points in predefined temperature steps. At each temperature the program calculates the total free energy curve. This free energy curve can then be processed as described herein, e.g., using the method 220, to determine a renormalized LLE curve. In an example implementation, a local addition to the COSMOTHERM® program (or other such program used to determine LLE), is configured to apply an embodiment of the present invention (e.g., CAFE renormalization equations 1-7 or CAFE subroutine as given above) and searches for the LLE points using a tangent procedure.

Figure 7:
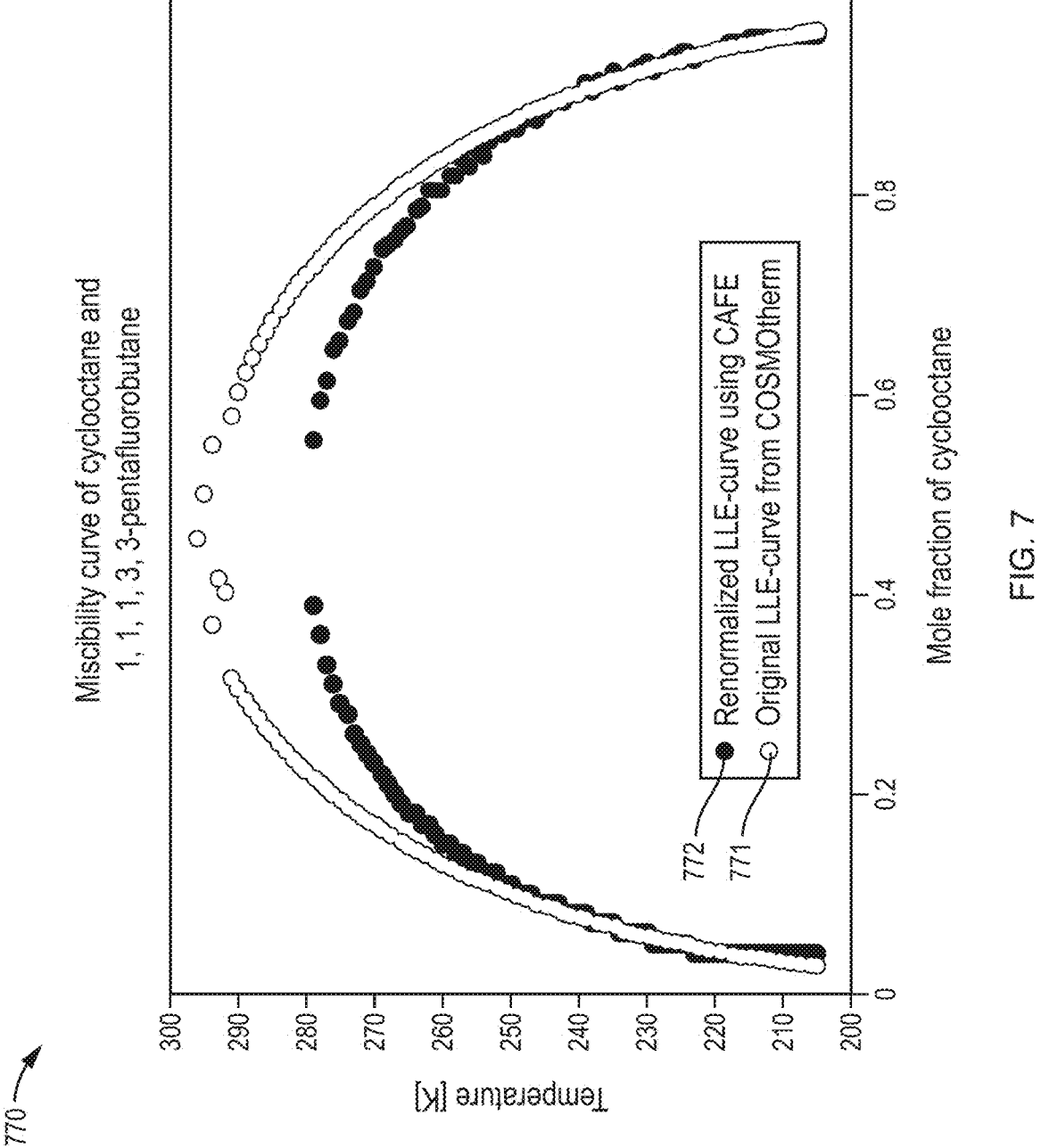
FIG. 7 is a plot of simulation results of the compounds of FIGS. 6A-C using an existing simulation technique and an embodiment of the present invention.

The plot 770 in FIG. 7 shows the unrenormalized miscibility curve 771 with the typical parabolic behavior near the UCST which is approximately 295 K. Applying embodiments of the present invention, e.g., CAFE renormalization procedures, upon the original free energy curves from COSMOTHERM®, yields the LLE curve 772 with the typical flat region close to the UCST, which now is 275.6 K. As such, by applying the example embodiment of the present invention, it is determined that the correct homogeneous temperature range reaches down to about 0° C., while unrenormalized COSMOTHERM® would have yielded about 22° C. as the lower limit of homogeneity. Based on this more precise prediction, a user can make better selections of promising refrigerants mixtures before tests are run in the lab.

Figure 8:
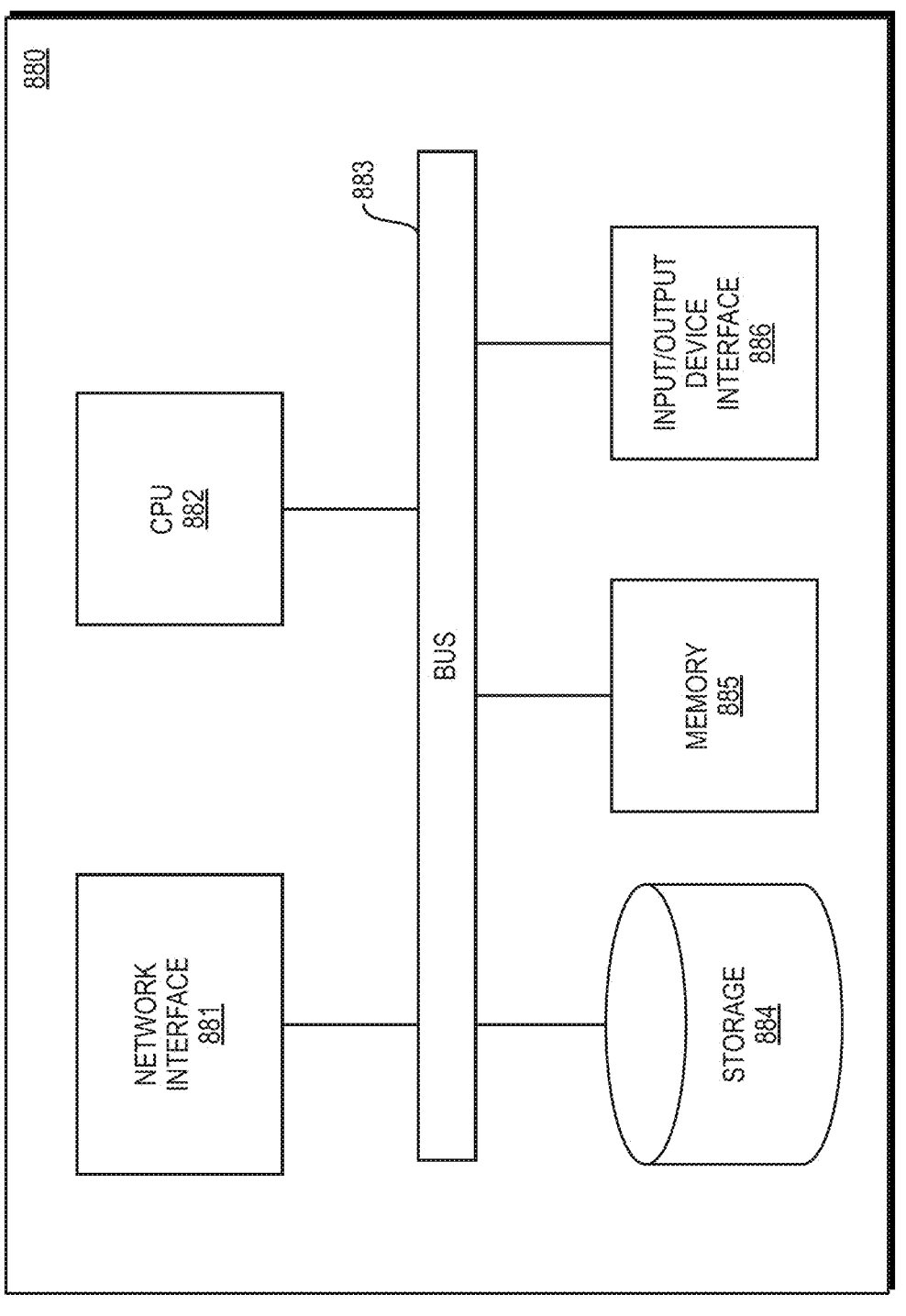
FIG. 8 is a simplified block diagram of a computer system for simulating a liquid mixture according to an embodiment.

FIG. 8 is a simplified block diagram of a computer-based system 880 that may be used to simulate a liquid mixture according to any variety of the embodiments of the invention described herein. The system 880 comprises a bus 883. The bus 883 serves as an interconnect between the various components of the system 880. Connected to the bus 883 is an input/output device interface 886 for connecting various input and output devices such as a keyboard, mouse, touch screen, display, speakers, etc. to the system 880. A central processing unit (CPU) 882 is connected to the bus 883 and provides for the execution of computer instructions. Memory 885 provides volatile storage for data used for carrying out computer instructions. Storage 884 provides non-volatile storage for software instructions, such as an operating system (not shown). The system 880 also comprises a network interface 881 for connecting to any variety of networks known in the art, including wide area networks (WANs) and local area networks (LANs).

It should be understood that the example embodiments described herein may be implemented in many different ways. In some instances, the various methods and machines described herein may each be implemented by a physical, virtual, or hybrid general purpose computer, such as the computer system 880, or a computer network environment such as the computer environment 990, described herein below in relation to FIG. 9. The computer system 880 may be transformed into the machines that execute the methods described herein, for example, by loading software instructions implementing method 220 into either memory 885 or non-volatile storage 884 for execution by the CPU 882. One of ordinary skill in the art should further understand that the system 880 and its various components may be configured to carry out any embodiments or combination of embodiments of the present invention described herein. Further, the system 880 may implement the various embodiments described herein utilizing any combination of hardware, software, and firmware modules operatively coupled, internally, or externally, to the system 880.

Figure 9:
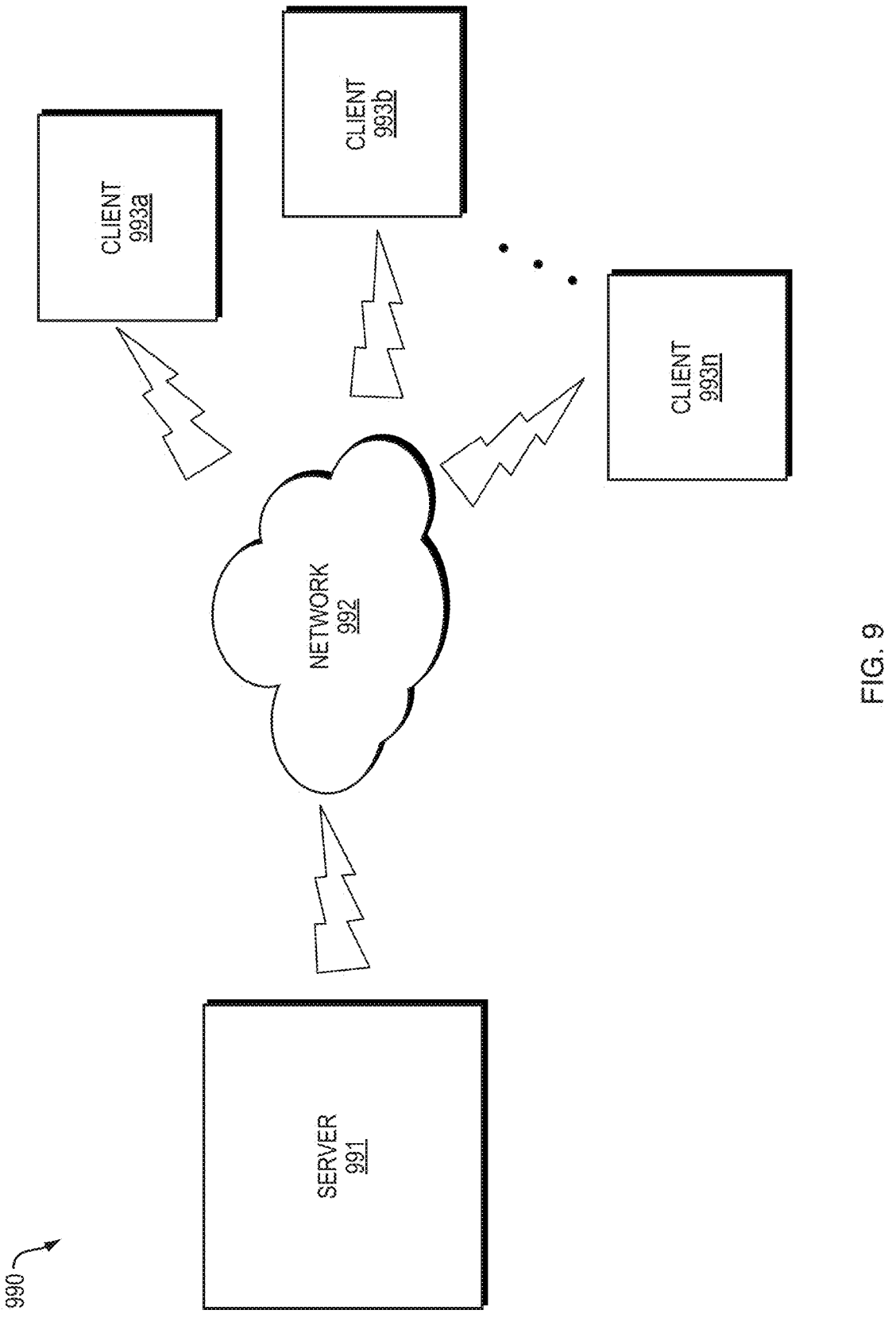
FIG. 9 is a simplified block diagram of a computer network environment in which embodiments of the present invention may be implemented.

FIG. 9 illustrates a computer network environment 990 in which an embodiment of the present invention may be implemented. In the computer network environment 990, the server 991 is linked through the communications network 992 to the clients 993a-n. The environment 990 may be used to allow the clients 993a-n, alone or in combination with the server 991, to execute any of the embodiments described herein. For non-limiting example, computer network environment 990 provides cloud computing embodiments, software as a service (SAAS) embodiments, and the like.

Embodiments or aspects thereof may be implemented in the form of hardware, firmware, or software. If implemented in software, the software may be stored on any non-transient computer readable medium that is configured to enable a processor to load the software or subsets of instructions thereof. The processor then executes the instructions and is configured to operate or cause an apparatus to operate in a manner as described herein.

Further, firmware, software, routines, or instructions may be described herein as performing certain actions and/or functions of the data processors. However, it should be appreciated that such descriptions contained herein are merely for convenience and that such actions in fact result from computing devices, processors, controllers, or other devices executing the firmware, software, routines, instructions, etc.

It should be understood that the flow diagrams, block diagrams, and network diagrams may include more or fewer elements, be arranged differently, or be represented differently. But it further should be understood that certain implementations may dictate the block and network diagrams and the number of block and network diagrams illustrating the execution of the embodiments be implemented in a particular way.

Accordingly, further embodiments may also be implemented in a variety of computer architectures, physical, virtual, cloud computers, and/or some combination thereof, and thus, the data processors described herein are intended for purposes of illustration only and not as a limitation of the embodiments.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

REFERENCES

[1] Wilson, K. G. Renormalization group and critical phenomena. II. Phase-space cell analysis of critical behavior. *Phys. Rev. B* 1971, 4, 3184-3205 (1971).
[2] Hohenberg, P. C., and A. P. Krekhov. "An introduction to the Ginzburg-Landau theory of phase transitions and nonequilibrium patterns." Physics Reports 572 (2015): 1-33.
[3] Walker, James S., and Chester A. Vause. "Lattice theory of binary fluid mixtures: Phase diagrams with upper and lower critical solution points from a renormalization-group calculation." The Journal of chemical physics 79.6 (1983): 2660-2676.
[4] Yu, Fan, and Jun Cai. "Renormalization Group Approach to Binary Liquid-Liquid Equilibria." Industrial & Engineering Chemistry Research 59.20 (2020).
[5] Hahn, Maximilian, and Klamt, Andreas. "Evaluation of cooperative correlation effects in lattice fluids with COSMOSPACE and COSMO-RSC based calculation models", (See document copy within the file wrapper, associated with the IDS filed Nov. 4, 2021).
[6] Klamt, Andreas, Gerard JP Krooshof, and Ross Taylor. "COSMOSPACE: Alternative to conventional activity coefficient models." AIChE journal 48.10 (2002).
[7] Lee, D. D., J. H. Choy, and J. K. Lee. "Computer generation of binary and ternary phase diagrams via a convex hull method." *Journal of phase equilibria* 13.4 (1992): 365-372.

What is claimed is:

1. A computer implemented method for screening liquid mixtures, the method comprising, by a processor:

receiving, in memory of the processor, a free energy curve of a liquid mixture comprising two components;

based on the received free energy curve, constructing a partition function describing fluctuations of mole fractions of the two components in the liquid mixture, wherein the partition function constructed covers symmetric and asymmetric fluctuations of the mole fractions of the two components around an average mole fraction;

using the constructed partition function, calculating a renormalized, with respect to the received free energy curve, free energy curve of the liquid mixture;

generating properties of the liquid mixture by performing a computer-based simulation of behavior of the liquid mixture using the calculated renormalized free energy curve, wherein the properties generated include at least one of: critical solution temperature, lower critical solution temperature, upper critical solution temperature, and renormalized equilibrium compositions of the two components of the liquid mixture; and screening the liquid mixture based on the properties generated.

2. The method of claim 1 wherein the renormalized free energy curve is a negative logarithm of the constructed partition function multiplied by molar thermal energy RT.

3. The method of claim 1 wherein the renormalized free energy curve is a function of a temperature scaling parameter.

4. The method of claim 3 wherein the temperature scaling parameter is a constant or a function of properties determined based on the received free energy curve of the liquid mixture.

5. The method of claim 1 wherein performing the computer-based simulation of behavior of the liquid mixture using the calculated renormalized free energy curve includes:

generating liquid-liquid-equilibrium of the liquid mixture using a tangent construction method.

6. A system for screening liquid mixtures, the system comprising:

a processor; and a memory with computer code instructions stored thereon, the processor and the memory, with the computer code instructions, being configured to cause the system to:

receive a free energy curve of a liquid mixture comprising two components;

based on the received free energy curve, construct a partition function describing fluctuations of mole fractions of the two components in the liquid mixture, wherein the partition function constructed covers symmetric and asymmetric fluctuations of the mole fractions of the two components around an average mole fraction;

using the constructed partition function, calculate a renormalized, with respect to the received free energy curve, free energy curve of the liquid mixture;

generate properties of the liquid mixture by performing a computer-based simulation of behavior of the liquid mixture using the calculated renormalized free energy curve, wherein the properties generated include at least one of: critical solution temperature, lower critical solution temperature, upper critical solution temperature, and renormalized equilibrium compositions of the two components of the liquid mixture; and screen the liquid mixture based on the properties generated.

7. The system of claim 6 wherein the renormalized free energy curve is a negative logarithm of the constructed partition function multiplied by molar thermal energy RT.

8. The system of claim 6 wherein the renormalized free energy curve is a function of a temperature scaling parameter.

9. The system of claim 8 wherein the temperature scaling parameter is a constant or a function of properties determined based on the received free energy curve of the liquid mixture.

10. The system of claim 6 wherein to perform the computer-based simulation of behavior of the liquid mixture using the calculated renormalized free energy curve, the processor and the memory, with computer code instructions, are further configured to cause the system to:

generate liquid-liquid-equilibrium of the liquid mixture using a tangent construction method.

11. A computer program product for screening liquid mixtures, the computer program product executed by a server in communication across a network with one or more clients and comprising:

a non-transitory computer readable medium, the computer readable medium comprising program instructions, which, when executed by a processor, causes the processor to:

receive a free energy curve of a liquid mixture comprising two components;

based on the received free energy curve, construct a partition function describing fluctuations of mole fractions of the two components in the liquid mixture, wherein the partition function constructed covers symmetric and asymmetric fluctuations of the mole fractions of the two components around an average mole fraction;

using the constructed partition function, calculate a renormalized, with respect to the received free energy curve, free energy curve of the liquid mixture;

generate properties of the liquid mixture by performing a computer-based simulation of behavior of the liquid mixture using the calculated renormalized free energy curve, wherein the properties generated include at least one of: critical solution temperature, lower critical solution temperature, upper critical solution temperature, and renormalized equilibrium compositions of the two components of the liquid mixture; and screen the liquid mixture based on the properties generated.

12. The computer program product of claim 11 wherein the renormalized free energy curve is a negative logarithm of the constructed partition function multiplied by molar thermal energy RT.

13. The computer program product of claim 11 wherein the renormalized free energy curve is a function of a temperature scaling parameter.

14. The computer program product of claim 13 wherein the temperature scaling parameter is a constant or a function of properties determined based on the received free energy curve of the liquid mixture.

15. The computer program product of claim 11 wherein to perform the computer-based simulation of behavior of the liquid mixture using the calculated renormalized free energy curve, the program instructions cause the processor to:

generate liquid-liquid-equilibrium of the liquid mixture using a tangent construction method.

* * * * *